United States Patent [19]  [11] 4,397,836
Madrange et al.  [45] Aug. 9, 1983

[54] AEROSOL HAIR LACQUER COMPOSITION CONTAINING AS A PROPELLANT A MIXTURE OF TRIFLUOROMONOCHLOROETHANE AND CARBON DIOXIDE AND OR NITROUS OXIDE

[75] Inventors: Annie Madrange, Saint-Germain-en-Laye; Jean-Louis Refregier, Boussy St-Antoine, both of France

[73] Assignee: Societe Anonyme Dite: L'OREAL, Paris, France

[21] Appl. No.: 277,855

[22] Filed: Jun. 26, 1981

Related U.S. Application Data

[63] Continuation of Ser. No. 905,454, May 12, 1978, abandoned.

[30] Foreign Application Priority Data

May 17, 1977 [FR] France ................................ 77 15089

[51] Int. Cl.³ .......................... A61K 7/00; A61K 7/06
[52] U.S. Cl. ........................................ 424/47; 424/71; 424/DIG. 1; 424/DIG. 2
[58] Field of Search ............ 424/47, DIG. 1, DIG. 2, 424/71; 252/305

[56] References Cited

U.S. PATENT DOCUMENTS

| | | | |
|---|---|---|---|
| 3,925,542 | 12/1975 | Viout et al. | 424/47 |
| 3,966,404 | 6/1976 | Papantoniou et al. | 424/47 |
| 4,010,872 | 3/1977 | Lozano et al. | 424/47 |
| 4,036,241 | 7/1977 | Karg et al. | 424/47 |
| 4,059,688 | 11/1977 | Rosenberg et al. | 424/71 |
| 4,080,438 | 3/1978 | Pomot et al. | 424/47 |
| 4,174,295 | 11/1979 | Bargigia et al. | 424/47 |

OTHER PUBLICATIONS

Chem. Abst., vol. 80 (1974), 74262k.

Primary Examiner—Allen J. Robinson
Attorney, Agent, or Firm—Cushman, Darby & Cushman

[57] ABSTRACT

A sprayable aerosol hair lacquer composition packaged under pressure in an aerosol container comprises a synthetic polymer for fixing the hair, an aliphatic alcohol and as an aerosol propellant a mixture of trifluoromonochloroethane and carbon dioxide and/or nitrous oxide.

10 Claims, No Drawings

AEROSOL HAIR LACQUER COMPOSITION CONTAINING AS A PROPELLANT A MIXTURE OF TRIFLUOROMONOCHLOROETHANE AND CARBON DIOXIDE AND OR NITROUS OXIDE

This is a continuation of application Ser. No. 905,454 filed May 12, 1978 now abandoned.

The present invention relates to a cosmetic composition and more particularly to a sprayable hair lacquer composition for fixing the hair after, for example, a hair setting operation or after combing the hair, packaged under pressure in an aerosol container.

The present invention more particularly is directed to the use of, as the propellant for said sprayable aerosol hair lacquers, a mixture consisting of (a) trifluoromonochloroethane and (b) carbon dioxide and/or nitrous oxide.

Until recently there has been employed as the propellant in sprayable aerosol hair lacquers, fluorochlorinated hydrocarbons or a mixture thereof.

In particular, mixtures consisting of Freon 11, and Freon 12 and principally 50/50 or 60/40 mixtures of these compounds were employed as aerosol propellants.

Additionally, other fluorochlorinated hydrocarbons as well as mixtures thereof were also employed as propellants. Principal ones of these were Freons 22, 114 and 142b as well as mixtures thereof combined, optionally, with Freon 11 and 12. Representative of such mixtures were Freons 11/12/114, Freons 22/114 and Freons 12/22/114.

Although these various propellants provided good results when spraying the cosmetic resins on the hair, their use at the present appears to be coming more and more limited due to ecological reasons.

It was then proposed to replace these propellants by gases such as, for example, carbon dioxide or nitrous oxide.

However, it has been established that the use of these latter gases resulted in quite mediocre vaporization qualities, with excessive wetting power. Further, certain undesired inflammability characteristics of the hair lacquer compositions containing them developed.

Furthermore, the internal pressure of the containers housing such compositions was relatively high which presented certain disadvantages, principal amongst which was the necessity of using special equipment so as to reduce the flow rate of the composition on release from the container.

After long and systematic investigations and studies the applicants have now found that it is possible to formulate excellent aerosol lacquer compositions which do not exhibit the above noted disadvantages by employing as the propellant a mixture of (a) trifluoromonochloroethane, i.e., "Freon 133A" and (b) carbon dioxide or nitrous oxide.

This particular combination of Freon 133A and carbon dioxide or nitrous oxide has as far as the applicants are aware never been contemplated for use in the production of aerosol lacquers for fixing the hair. The use of the propellant mixture of the present invention makes it possible to improve significantly the vaporization qualities of the composition and to obtain a significant reduction of the wetting power.

Moreover, the use of the aerosol propellant mixture of the present invention makes it possible to reduce the internal pressure of the aerosol container to a not negligible degree, since in certain cases the internal pressure can be in the order of 3 bars.

Consequently by using the propellant mixture of the present invention it is not necessary to have recourse to special equipment. Accordingly, conventional aerosol valve systems, such as those provided on aerosol containers designed for the use of conventional propellants such as, for example, a mixture of Freon 11 and Freon 12, can be employed.

Moreover it has now been established that the use of Freon 133A, even in relatively weak concentrations, can reduce to a significant degree the inflammability characteristics of compositions propelled with carbon dioxide or nitrous oxide.

In effect, the applicants have found that by using an amount in the order of 10% Freon 133A, it is possible to reduce the inflammability characteristics of the hair lacquer composition and that these characteristics can be practically completely suppressed by progressively increasing the amount of "Freon 133A" in the propellant mixture.

Thus, the present invention relates to a sprayable aerosol lacquer for fixing the hair packaged under pressure in an aerosol container comprising (i) at least one synthetic polymer or cosmetic resin for fixing the hair, (ii) at least one aliphatic alcohol having from 2-4 carbon atoms, (iii) from 0 to 40 weight percent of at least a third or auxiliary solvent, (iv) from 0 to 20 weight percent water, and (v) a propellant mixture consisting of (a) trifluoromonochloroethane ("Freon 133A") in an amount of 5 to 80 weight percent and (b) a sufficient amount of carbon dioxide or nitrous oxide so that the internal pressure of said container is between 3 and 8 bars and preferably between 4 and 6 bars.

In accordance with the present invention, the synthetic polymer or cosmetic resin is present in the hair lacquer composition in an amount between 0.5 and 10 weight percent thereof.

Representative synthetic polymers or cosmetic resins that can be employed in the aerosol hair lacquer composition of this invention include in particular: polyvinylpyrrolidone known under the name of "PVP K30" (molecular weight=40,000) sold by GAF; copolymers of vinylpyrrolidone and vinyl acetate known (i) under the commercial names of "PVP/VA E335, S630 and E535," sold by GAF, E335 being 30% vinylpyrrolidone/70% vinyl acetate, S630 being 60% vinylpyrrolidone/40% vinyl acetate and E535 being 50% vinylpyrrolidone/50% vinyl acetate; and (ii) under the commercial names of "Luviskol VA37E, VA64 and VA281" sold by BASF, VA37E being 30% vinylpyrrolidone/70% vinyl acetate, VA64 being 60% vinylpyrrolidone/40% vinyl acetate, and VA281 being 20% vinylpyrrolidone/80% vinyl acetate; copolymers of vinyl acetate and crotonic acid sold under the commercial names of (i) "Resin 28-13-10", polyvinyl acetate/carboxylic acid copolymers (90/10 vinyl acetate-crotonic acid copolymer, (ii) "Aresil 86.12" and (iii) "Aristoflex C"; copolymers of methyl vinyl ether/maleic anhydride semiesterified with a lower aliphatic alcohol such as methanol, ethanol, butyl alcohol or isopropyl alcohol and in particular copolymers known under the commercial names of "Gantrez ES225, ES335I and ES425", sold by GAF, "ES225" being the monoethyl ester of the copolymer of methyl vinyl ether/maleic anhydride, "ES 3351" being the monoisopropyl ester of the methyl vinyl ether/maleic anhydride copolymer and "ES425" being the monobutyl ester of methyl vinyl ether/maleic anhydride copolymer; amphoteric acrylic copolymers sold under the commercial name of "Amphomer"; vinyl terpolymers with acrylic and carboxylic ester groups sold under the commercial names of VEM640 and 649"; terpolymers of vinyl acetate, crotonic acid and vinyl neodecanoate sold under the commercial name of "Resine 28.2930"; as well as the polymers described in the following U.S. Pat. Nos. 3,925,542 and 3,966,404.

All the copolymers carrying free carboxylic acid functions generally are utilized in the neutralized form, i.e. they are neutralized to an amount of 10 to 100% with an organic base such as 2-amino-2-methyl propanediol-1,3,2-amino-2-methyl propanol-1, triisopropanolamine, and the like.

It will be noted that while these polymers or resins have very different structures, they can be used indifferently in the aerosol hair lacquer composition of the present invention without causing incompatability with the propellant mixture. No instance of the phenomenon of valve closing or clogging has been observed using these various polymers in the present invention.

The aliphatic alcohol employed as the solvent in this invention is present in an amount between 5 and 79.5 weight percent and preferably between 10 and 69.5 weight percent.

Representative aliphatic alcohols that can be used in the aerosol hair lacquer compositions of the present invention include, in particular, ethanol, isopropanol, butanol and propanol.

The trifluoromonochloroethane, i.e. "Freon 133A" which is employed in the propellant mixture composition has the chemical formula: $F_3C-CH_2Cl$, the molecular mass of which is 118.42. It is a liquified gas under pressure, inflammable, non-corrosive and non-toxic. Its boiling point is 5.4° C. under a 760 mm Hg.

In accordance with a first and preferred embodiment of the present invention, the aerosol hair lacquer contains at least a third or auxiliary organic solvent selected from the group consisting of methylene chloride, trichloroethane, ethyl chloride, acetone, ethyl acetate, pentane, hexane or dichlorodifluoroethane.

In accordance with this particular embodiment, the third or auxiliary solvent can be present in the hair lacquer composition in a maximum amount of 40 weight percent. Preferably it is present in an amount between 10 and 35 weight percent.

In accordance with a second particular embodiment of the present invention, the aerosol hair lacquer composition can contain water in a maximum amount of 20 weight percent. Preferably it is present in an amount between 0.5 and 6 weight percent.

When the hair lacquer composition according to the invention contains water in an amount of 0.5 to 6%, it is also preferable not to use as the third or auxiliary solvent one which is chlorinated or at least to use such a chlorinated solvent in an amount as small as possible.

Moreover, the hair lacquer composition of the present invention can also contain other conventional cosmetic components such as plasticizers, neutralizing agents, hair shining agents, perfumes, dyes and the like.

The following non-limiting examples illustrate the present invention. Unless otherwise stated, all parts and percentages are by weight.

EXAMPLE I

An aerosol hair lacquer packaged in an aerosol container is produced by admixing the following components:

| | |
|---|---|
| Gantrez ES225, sold by GAF | 2.7 g |
| Triisopropanolamine | 0.3 g |
| Lanolin plasticizer | 0.5 g |
| Ethanol | 51.5 g |
| Freon 133A | 35 g |
| Nitrous oxide, sufficient for an internal pressure of the container of 7 bars (approximately 10g) | |

EXAMPLE II

An aerosol hair lacquer, packaged in an aerosol container, is produced by admixing the following components:

| | |
|---|---|
| Resin 28-13-10 | 3 g |
| 2-amino-2-methyl propanediol-1,3 | 0.3 g |
| Ethanol | 18 g |
| Freon 133A | 75 g |
| Nitrous oxide, sufficient for an internal pressure of said container of 4 bars | |

EXAMPLE III

An aerosol hair lacquer composition packaged in an aerosol container is produced by admixing the following components:

| | |
|---|---|
| "Amphomer" resin | 3 g |
| 2-amino-2-methyl propanol-1 | 0.5 g |
| Methylene chloride | 35 g |
| Silicone SF 1075, plasticizer | 0.4 g |
| Ethanol | 44.1 g |
| Freon 133A | 10 g |
| Carbon dioxide, sufficient for an internal pressure of the container of 7 bars | |

EXAMPLE IV

An aerosol hair lacquer composition packaged in an aerosol container is produced by admixing the following components:

| | |
|---|---|
| Resin 28-13-10 | 4.5 g |
| 2-amino-2-methyl propanol-1 | 0.5 g |
| Isopropylan 33 plasticizer (isopropanol ester of lanolin) | 0.5 g |
| Trichloroethane | 35 g |
| Ethanol | 15 g |
| Freon 133A | 40 g |
| Nitrous oxide, sufficient for an internal pressure of the container of 4 bars | |

What is claimed is:

1. In a sprayable hair lacquer composition packaged under pressure in an aerosol container comprising
   (i) an effective amount of a synthetic polymer for fixing the hair,
   (ii) an effective amount of an aliphatic alcohol having from 2-4 carbon atoms, (iii) from 0 to 40 weight percent of an auxiliary solvent,
(iv) from 0 to 20 weight percent water, and
(v) a propellant, the improvement comprising as a propellant a mixture consisting essentially of (a) trifluoromonochloroethane in an amount from 5 to 80 weight percent of said composition and (b) nitrous oxide in an amount sufficient so that the internal pressure of said container is between 3 and 8 bars.

2. The hair lacquer composition of claim 1 wherein said synthetic polymer is present in an amount between 0.5 and 10 weight percent.

3. The hair lacquer composition of claim 1 wherein said aliphatic alcohol is present in an amount between 5 and 79.5 weight percent.

4. The hair lacquer composition of claim 1 wherein said aliphatic alcohol is present in an amount between 10 and 69.5 weight percent.

5. The hair lacquer composition of claim 1 wherein said aliphatic alcohol is selected from the group consisting of ethanol, isopropanol, butanol and propanol.

6. The hair lacquer composition of claim 1 wherein said auxiliary solvent is present in an amount between 10 and 35 weight percent.

7. The hair lacquer composition of claim 1 wherein said auxiliary solvent is selected from the group consisting of methylene chloride, trichloroethane, ethyl chloride, acetone, ethyl acetate, pentane, hexane and dichlorodifluoroethane.

8. The hair lacquer composition of claim 1 wherein water is present in an amount between 0.5 and 6 weight percent.

9. The hair lacquer composition of claim 1 wherein the internal pressure of the aerosol container is about 4 to 6 bars.

10. The hair lacquer composition of claim 1 which also includes one or more of a plasticizer, a neutralizing agent, a hair shining agent, a perfume and a dye.

* * * * *